United States Patent [19]
Fertel et al.

[11] Patent Number: 5,773,668
[45] Date of Patent: Jun. 30, 1998

[54] METHOD OF MAKING TRICHLOROMETHOXYBENZENE

[75] Inventors: Lawrence Fertel, Williamsville; Michael Fifolt; Mary Cocoman, both of Grand Island; Walter Opalinski, Tonawanda; William Derwin, Buffalo, all of N.Y.

[73] Assignee: Occidental Chemical Corporation, Niagara Falls, N.Y.

[21] Appl. No.: 805,393

[22] Filed: Feb. 24, 1997

[51] Int. Cl.$^6$ ............................................. C07C 85/14
[52] U.S. Cl. ................... 568/655; 568/656; 204/157.48; 204/157.64
[58] Field of Search ................... 568/655, 656; 204/157.48, 157.64

[56] References Cited

U.S. PATENT DOCUMENTS 5,440,051  8/1995  Marhold et al. .
5,484,932  1/1996  Marhold .

OTHER PUBLICATIONS

"Formation of Dichloromethyl Phenyl Ethers As Major Products In The Photo–Reimer–Tiemann Reaction Without Base," by M. Consuelo Jimenez et al, in Tetrahedron, vol. 51, No. 20, pp. 5825–5830 (1995).

"Selective Side–Chain Chlorination of Methoxybenzenes," by Robert Louw and Peter W. Franken, in Chemistry and Industry (London), No. 3, pp. 127 Feb. 5, 1977.

"Photochemical Chlorination With Sulfuryl Chloride VII.* Chlorination of Anisole," by M. G. Voronkov et al., translated from Zhurnal Organicheskoi Khimii, vol. 7, No. 7, pp. 1438–1440, Jul., 1971.

Curran et al; J.Org.Chem. 62, 450–451, 1997.

*Primary Examiner*—Gary Geist
*Assistant Examiner*—Sreeni Padmanabhan
*Attorney, Agent, or Firm*—Richard D. Fuerle

[57] ABSTRACT

Disclosed is a method of making trichloromethoxybenzene. A mixture is prepared of anisole and a source of chlorine free radicals, such as chlorine or sulfuryl chloride. The reaction is performed in a solvent, which can be either benzotrifluoride, orthochlorobenzotrifluoride, metachlorobenzotrifluoride, parachlorobenzotrifluoride, or dichlorobenzotrifluoride. The mixture is exposed to actinic radiation, such as ultraviolet light, which generates the chlorine free radicals.

21 Claims, No Drawings

METHOD OF MAKING TRICHLOROMETHOXYBENZENE

BACKGROUND OF THE INVENTION

This invention relates to a method of making trichloromethoxybenzene by reacting anisole with a source of chlorine free radicals in the presence of actinic radiation. In particular, it relates to the use of solvents based on benzotrifluoride in that reaction.

Trichloromethoxybenzene has been made by reacting anisole with gaseous chlorine in the presence of ultraviolet light. This reaction was performed in the presence of carbon tetrachloride. However, carbon tetrachloride has been found to be toxic and an ozone depleter and its use is now heavily taxed and regulated. Efforts are being made to find a substitute solvent.

SUMMARY OF THE INVENTION

We have discovered that anisole can be photochlorinated without significant chlorination of the aromatic ring if the solvent used is based on benzotrifluoride (BTF), $\alpha,\alpha,\alpha$-trifluoromethylbenzene. While the use of no solvent or other common solvents results in significant chlorination of the aromatic ring, when the reaction is performed using a solvent according to this invention, less than about 5 mole % of the aromatic ring is are chlorinated.

We have further discovered that chlorination of the anisole aromatic ring can be still further reduced by adding the anisole and the chlorine separately to the solvent. We have no explanation for this unexpected improvement.

DESCRIPTION OF THE PREFERRED EMBODIMENTS

In the method of this invention, anisole is reacted with chlorine free radicals in a BTF solvent to produce trichloromethoxybenzene (TCMB). If chlorine is used, the reaction is:

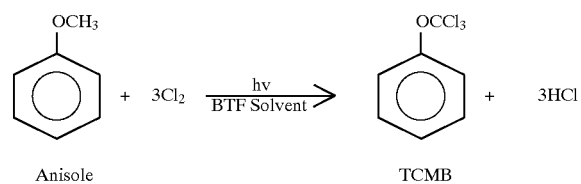

Anisole is a liquid which can be mixed with about 10 to about 70 wt % of the BTF solvent in order to control the rate of reaction. At least about 10 wt % anisole (based on total solvent plus anisole weight) should be used for an economical process, and if the weight % of anisole is greater than about 60, ring chlorination may begin to occur. Preferably, the concentration of anisole is about 30 to about 50 wt %.

The source of chlorine free radicals can be, for example, elemental gaseous or liquified chlorine or liquid sulfuryl chloride ($SO_2Cl_2$). Gaseous chlorine is preferred as it results in fewer byproducts, it is inexpensive, and it works well. At least a stoichiometric amount of the source of chlorine free radicals is needed (i.e., 3 moles $Cl_2$ per mole of anisole), but a slight (1 to 5 mole %) excess is preferred to insure a complete reaction and reduce ring chlorination.

BTF solvents that can be used in this invention include BTF, orthochlorobenzotrifluoride, metachlorobenzotrifluoride, parachlorobenzotrifluoride (PCBTF), and dichlorobenzotrifluoride. BTF and PCBTF are preferred as they have been found to work well. The use of these solvents is essential to reducing ring chlorination.

The anisole, solvent, and chlorine free radical source can be mixed together in any fashion such as, for example, adding the chlorine free radical source to a mixture of the anisole and the solvent, adding the anisole and the chlorine free radical source separately to the solvent, or mixing some of the solvent with the anisole first, then adding that mixture and the chlorine free radical source separately to a solvent. For some unknown reason, it has been found that if the anisole and the chlorine free radical source are kept apart until they are mixed with the solvent, ring chlorination is reduced.

It has also been found that ring chlorination increases at lower temperatures and therefore it is preferable to perform the reaction at as high a temperature as is practical. Generally, therefore, it is preferable to reflux the solvent during the reaction; this reduces ring chlorination by removing hydrogen chloride. For benzotrifluoride, the reaction would be performed at about 105° C. and for parachlorobenzotrifluoride, the reaction would be performed at about 136° C.

Any actinic radiation, i.e., radiation that will produce chlorine free radicals, such as by the reaction

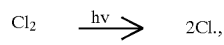

can be used. Examples of actinic radiation include, for example, ultraviolet light, radio frequency, x-rays, or free radical initiators. Ultraviolet light is preferred as it is convenient and easy to use. An ultraviolet wavelength of about 320 to about 340 nm is suitable. Since the light does not penetrate deeply into the mixture, the light source should be placed as close to the mixture as possible. This can be accomplished, for example, by placing the light in a well which is inside the reactor. The mixture should be stirred to expose all portions of the mixture to the light to ensure continuous generation of chlorine free radicals.

If the reaction mixture is in contact with a metal, it may be desirable to add about 5 to about 500 ppm (based on mixture weight) of a metal scavenger to the mixture to prevent the metal ions from catalyzing the production of byproducts. Examples of suitable metal scavengers include N,N-dialkylalkyl amides (sold as "Hallcomid" by the C. P. Hall company) and ethylenediaminetetraacetic acid (EDTA).

The reaction can be performed as a batch, continuous, or semi-continuous process, but a continuous process is preferred as it is more efficient and is more likely to result in less ring chlorination. It is also possible to partially chlorinate the anisole to a mixture of mono-, di- and trichloromethoxybenzenes in a continuous process, and then transfer the mixture to a batch reactor to finish off the chlorination. In a preferred continuous process, the anisole and the chlorinating agent are added separately to a stream moving past a source of ultraviolet light. The rate of addition to the stream in a continuous process should be selected to optimize the reaction.

The trichloromethoxybenzene product is useful as a chemical intermediate. For example, it can be reacted with hydrogen fluoride to make trifluoromethoxybenzene, which can be used to make herbicides and pecticides. The following examples further illustrate this invention. Unless otherwise specified, the reactor used was a 350 mL photochlorination apparatus equipped with a 100 W medium pressure Hanovia UV light (air cooled), a reflux condenser, thermometer and an inlet for chlorine.

COMPARATIVE EXAMPLE 1

Reaction in Freon 113

Into the reactor was placed 71 g of anisole and 400 mL of 1,2-dichlorotrifluroethane, sold by Dupont as "Freon 113"

(the solvent), along with 500 ppm of a mixture of 5 wt % N,N-dimethyl caproamide, 50 wt % N,N-caprylamide, 40 wt % N,N-capramide, and 5 wt % N,N-dimethyl lauramide, sold by The C. P. Hall Company as "Hallcomid M 8-10" (a metal sequesterer). The reactor was heated to reflux (50° C.), the light was turned on, and chlorine was sparged in. Gas chromatography (GC) analysis indicated the formation of 36.1 wt % undesired by-products, consisting predominantly of ring chlorinated materials. Side chain chlorinated materials were formed in 63.9 wt % yield, as a mixture of mono-, di-, and trichloromethoxybenzenes.

COMPARATIVE EXAMPLE 2

Reaction in Glacial Acetic Acid

Into the reactor was placed 53.1 g of anisole and 250 mL of glacial acetic acid, along with 500 ppm of "Hallcomide M8-10." The reactor was heated to reflux (122° C.), the light was turned on, and chlorine was sparged in. GC analysis indicated the formation of 36.1 wt % undesired by-products, consisting predominantly of ring chlorinated materials. No desired product was formed.

COMPARATIVE EXAMPLE 3

Reaction with No Added Solvent

Into the reactor was placed 292 g of anisole, along with 500 ppm of "Hallcomide M8-10." The reactor was heated to reflux (133° C.), the light was turned on, and chlorine was sparged in. GC analysis indicated the formation of 44.9 wt % ring chlorinated material, with 24.6% side chain chlorinated materials as a mixture of mono- and dichloromethoxybenzenes along with 30.5% unreacted anisole.

COMPARATIVE EXAMPLE 4

Reaction Neat with Added Phosphorus Trichloride

Into the reactor was placed 284 g of anisole, along with 500 ppm of "Hallcomide M8-10" and 1.0 g of phosphorus trichloride. The reactor was heated to reflux (136° C.), the light was turned on, and chlorine was sparged in. GC analysis indicated the formation of 27.3 wt % ring chlorinated material, a 26.5 wt % yield of side chain chlorinated materials, as a mixture of mono- and dichloromethoxybenzenes, and 46.2 wt % unreacted anisole.

COMPARATIVE EXAMPLE 5

Reaction with Benzotrichloride

Into the reactor was placed 53 g of anisole and 250 mL of benzotrichloride ($\alpha,\alpha,\alpha$-trichloromethylbenzene), along with 500 ppm of "Hallcomide M8-10." The reactor was heated to reflux (136° C.), the light was turned on, and chlorine was sparged in. The solution became dark upon photolysis, and the reaction was stopped immediately.

Comparative Examples 1 to 5 show that certain solvents are unacceptable in the photochlorination of anisole because they lead to high levels of ring chlorinated product along with other byproducts. Photochlorination reactions run in the absence of solvent also lead to unacceptable levels of ring chlorination.

Reactions in which the anisole and solvent are added together at the beginning of the reaction.

EXAMPLE 1

Reaction in Benzotrifluoride (BTF)

Into the reactor was placed 53 g of anisole and 250 mL of BTF along with 500 ppm of "Hallcomide M8-10." The reactor was heated to reflux (108° C.), the light was turned on, and chlorine was sparged in at 120 mL/min for 5 hours. GC analysis indicated the complete consumption of anisole and the formation of trichloromethoxybenzene in an 83.9 wt % yield. There was 15.7 wt % ring chlorinated products, and 0.4 wt % of dichloromethoxybenzene remaining.

EXAMPLE 2

Reaction in Parachlorobenzotrifluoride (PCBTF)

Into the reactor was placed 53 g of anisole and 250 mL of parachlorobenzotrifluoride (4-chloro-$\alpha,\alpha,\alpha$-trifluoromethylbenzene) along with 500 ppm of "Hallcomide M8-10." The reactor was heated to reflux (135° C.), the light was turned on, and chlorine was sparged in at 120 mL/min for 5 hours. GC analysis indicated the complete consumption of anisole and the formation of trichloromethoxybenzene in an 92.8 wt % yield. There was 7.2 wt % ring chlorinated products present.

Examples 1 and 2 show that anisole pre-mixed in BTF solvents prior to chlorination under free radical conditions leads to high yields of the desired trichloromethoxybenzene product.

In Examples 3 to 12, anisole and the solvent (in all cases PCBTF) were added together at the beginning of the reaction. The chlorine addition time is the time in which the theoretical amount of chlorine (3 moles per mole of anisole) had been added.

| Example | % Anisole (wt/wt) | Temperature (°C.) | ppm Hallco-mide | Chlorine Addition time (hr.) | % Side chain chlorinated products | % Ring chlorinated products |
|---|---|---|---|---|---|---|
| 3 | 30 | 135 | 0.1 | 10 | 77.8 | 22.2 |
| 4 | 30 | 80 | 0.5 | 10 | 4.5 | 95.5 |
| 5 | 15 | 135 | 0.5 | 5 | 88.5 | 11.5 |
| 6 | 15 | 135 | 0.1 | 10 | 85.8 | 14.2 |
| 7 | 30 | 107 | 0.1 | 5 | 24.2 | 75.8 |
| 8 | 15 | 90 | 0.1 | 5 | 35.5 | 64.5 |
| 9 | 30 | 80 | 0.1 | 5 | 7.2 | 92.8 |
| 10 | 15 | 80 | 0.1 | 5 | 2.8 | 97.2 |
| 11 | 15 | 80 | 0.5 | 10 | 10.8 | 89.2 |
| 12 | 30 | 135 | 0.5 | 5 | 73.3 | 26.7 |

Examples 3 to 12 show that higher temperatures (Examples 3, 5, 6, and 12) lead to higher levels of side chain chlorinated products than reactions run at lower temperatures.

Reactions in which anisole is added concomitantly with chlorine to the solvent.

EXAMPLE 13

Reaction in PCBTF

Into the reactor was placed 124 mL of PCBTF along with 600 ppm of "Hallcomide M8-10." The reactor was heated to reflux (135° C.), the light was turned on, and chlorine and anisole were added together. The chlorine was added at a rate of 42 g/hr. The anisole (125 g, 50% by weight of PCBTF) was also added at a rate of 42 g/hr. Once all of the anisole had been added, additional chlorine was sparged in until the reaction was complete. An assay by GC showed 94.2 wt % desired trichloromethoxybenzene, with 5.7 wt % ring chlorinated material. No anisole was present.

EXAMPLE 14

Reaction in BTF

In a 3 L photochlorination apparatus equipped with a 100 W medium pressure Hanovia UV light (air cooled, Pyrex filter inside the light well), a reflux condenser, a funnel for the addition of anisole, a thermometer and an inlet for chlorine was placed 1500 g of BTF. The reactor was heated to reflux (105° C.), the light was turned on, and chlorine and anisole were added together. The chlorine was added at a rate of 1200 mL/min. The anisole (1500 g, 50% by weight of PCBTF) was added at a rate of 150–200 g/hr. When all of the anisole had been added, additional chlorine was added to complete the reaction. An assay by GC showed 87.8 wt % desired trichloromethoxybenzene, 1.9 wt % dichloromethoxybenzene, and 10.3 wt % ring chlorinated material. No anisole was present.

The following experiments summarize results in which anisole and chlorine were added at the same time to the reaction at the reflux temperature of the solvent (105° C. for BTF, 135° C. for PCBTF). In the following table, the percent solution is weight/weight percent anisole/solvent, the anisole add time is the time it took to completely add the anisole into the solvent, the chlorine rate is in standard cubic centimeters per minute, the light used is either a 100 or 400 watt medium pressure Hanovia lamp, the % side and ring products were analyzed by GC, and the reaction scale was the size of the photochemical reactor used.

| Ex. | Solvent Used | Percent Solution (wt/wt) | ppm Hallcomid | Anisole Add Time | Chlorine Rate (sccm) | % Anisole Remaining | % Side Chain Products | % Ring Products | Light Used | Reaction Scale | Comments |
|---|---|---|---|---|---|---|---|---|---|---|---|
| 15 | PCBTF | 30 | 600 | 3.0 hr. | 55 | 23 | 61.2 | 15.8 | 100 w | 350 | Run Complete |
| 16 | PCBTF | 15 | 600 | 3.0 hr. | 60–120 | 0 | 96.3 | 3.7 | 100 w | 350 | Run Complete |
| 17 | PCBTF | 30 | 600 | 3.0 hr. | 150–200 | 0 | 85.8 | 14.2 | 100 w | 350 | Run Complete |
| 18 | PCBTF | 30 | 600 | 3.0 hr. | 175–200 | 0 | 92.1 | 7.9 | 100 w | 350 | Run Complete |
| 19 | PCBTF | 50 | 600 | 3.0 hr. | 175–275 | 0 | 94.3 | 5.7 | 100 w | 350 | Run Complete |
| 20 | PCBTF | 30 | 600 | 3.0 hr. | 175–275 | 0 | 94.0 | 6.0 | 100 w | 350 | Run Complete |
| 21 | PCBTF | 50 | 50 | 3.0 hr. | 225–325 | 0 | 79.0 | 21.0 | 100 w | 350 | Believed to have too light of a reflux |
| 22 | PCBTF | 50 | 300 | 3.0 hr. | 225–325 | 10.5 | 72.9 | 16.6 | 100 w | 350 | Believed to have too light of a reflux |
| 23 | PCBTF | 50 | 300 | 3.0 hr. | 225–325 | 0 | 86.7 | 13.7 | 100 w | 350 | Repeated #22 with harder reflux |
| 24 | PCBTF | 50 | 300 | 3.0 hr. | 1400–1700 | 0 | 63.4 | 36.6 | 100 w | 3000 | Run Complete |
| 25 | PCBTF | 50 | 300 | 4.0 hr. | 1000–1700 | 0 | 68.9 | 31.1 | 400 w | 3000 | Strip-off overhead while adding anisole |
| 26 | PCBTF | 50 | 600 | 3.0 hr. | 175–275 | 0 | 74.4 | 25.6 | 100 w | 350 | |
| 27 | PCBTF | 21 | 600 | 2.0 hr. | 175–275 | 0 | 93.8 | 6.2 | 100 w | 350 | Run Complete |
| 28 | PCBTF | 50 | 600 | 3.0 hr. | 175–275 | 0 | 89.8 | 11.2 | 100 w | 350 | Run Complete |
| 29 | PCBTF | 50 | 600 | 3.0 hr. | 275–400 | 0 | 89.2 | 11.8 | 100 w | 350 | Same as #28 except faster Cl2 rate |
| 30 | PCBTF | 50 | 600 | 4.5 hr. | 900–1500 | 0 | 61.9 | 38.1 | 100 w | 3000 | Run Complete |
| 31 | PCBTF | 50 | 600 | 8.0 hr. | 200–300 | 16.4 | 59.1 | 24.5 | 100 w | 3000 | Initial ~12% anisole added -then as above |
| 32 | BTF | 50 | 0 | 3.0 + 2.0 hr. | 175–275 | 0 | 89.0 | 11.0 | 100 w | 350 | 30% Anisole addition- then upped to 50% |
| 33 | PCBTF | 30 | 600 | 4.5 hr. | 100–275 | 0.25 | 71.41 | 28.32 | 100 w | 350 | Run Complete |
| 34 | PCBTF | 50 | 600 | Aborted | 175 | 15.07 | 10.59 | 74.34 | 100 w | 350 | Triphenylphosphine added. Run aborted. |
| 35 | PCBTF | 30 | 600 | 3.5 hr. | 175 | 18.96 | 32.00 | 49.04 | 100 w | 350 | Run complete |
| 36 | PCBTF | 30 | 500 | 3.5 hr. | 175–150 | 0 | 93.13 | 6.87 | 100 w | 350 | Run complete |
| 37 | PCBTF | 30 | 500 | 4.5 hr. | 175 | 0 | 85.79 | 14.21 | 100 w | 350 | Run complete |
| 38 | PCBTF | 30 | 0 | 5.0 hr. | 175 | 0 | 93.04 | 6.96 | 100 w | 350 | Run complete |
| 39 | PCBTF | 50 | 0 | 8.5 hr. | 175–150 | 0 | 71.14 | 28.86 | 100 w | 350 | Run aborted |
| 40 | BTF | 23 | 0 | 6.5 hr. | 1100 | 0 | 84.9 | 15.1 | 100 w | 3 L | Lower air flow around well |
| 41 | BTF | 23 | 0 | 5.5 hr. | 1100 | 0 | 94.6 | 5.4 | 100 w | 3 L | High air flow around light well |
| 42 | BTF | 23 | 0 | 5 hr. | 1200–1400 | 0 | 97.2 | 2.8 | 100 w. | 3 L | Pyrex filter used, no scum around light well noticed |
| 43 | BTF | 41 | 0 | 7 h | 1300 | 0 | 82.2 | 17.8 | 100 w. | 3 L | Pyrex filter used, added anisole too fast. |
| 44 | BTF | 50 | 0 | 12 h | 1200 | 0 | 89.7 | 10.3 | 100 w. | 3 L | Pyrex filter used, was at 95% when light went out |

Examples 13 to 44 show that co-addition of anisole and chlorine to a refluxing solution of BTF solvents under free radical generating conditions under different process variables such as chlorine flow, temperature, and concentration leads to good selectivities and yields of trichloromethoxybenzene.

We claim:

1. A method of making trichloromethoxybenzene comprising
   (A) preparing a mixture of anisole and a source of chlorine free radicals in a solvent selected from the group consisting of benzotrifluoride, orthochlorobenzotrifluoride, metachlorobenzotrifluoride, parachlorobenzotrifluoride, and dichlorobenzotrifluoride;
   (B) heating said mixture to the reflux temperature of said solvent: and
   (C) generating said chlorine free radicals in said mixture.

2. A method according to claim 1 wherein said source of free radicals is selected from the group consisting of chlorine and sulfuryl chloride.

3. A method according to claim 2 wherein said source of chlorine free radicals is chlorine gas.

4. A method according to claim 1 wherein said solvent is benzotrifluoride.

5. A method according to claim 1 wherein said solvent is parachlorobenzotrifluoride.

6. A method according to claim 1 including the additional last step of reacting said trichloromethoxybenzene with hydrogen fluoride to produce trifluoromethoxybenzene.

7. A method according to claim 1 wherein said source of chlorine free radicals is added to a mixture of said anisole and said solvent.

8. A method according to claim 1 wherein said anisole and said source of chlorine free radicals are added separately to said solvent.

9. A method according to claim 8 wherein a small amount of said anisole is first mixed with said solvent.

10. A method according to claim 1 wherein the amount of anisole is about 10 to about 60 wt % of the total weight of anisole and solvent.

11. A method according to claim 1 wherein, when said process is performed in contact with metal, about 5 to about 500 ppm of a metal scavenger is added to said mixture.

12. A method of making trichloromethoxybenzene comprising
    (A) preparing a mixture of
       (1) about 30 to about 50 wt % anisole;
       (2) about 50 to about 90 wt % benzotrifluoride or parachlorobenzotrifluoride; and
       (3) at least a stoichiometric amount of chlorine gas;
    (B) heating said mixture to about reflux; and
    (C) irradiating said mixture with ultraviolet light of an energy sufficient to form chlorine free radicals.

13. A method according to claim 12 wherein said solvent is benzotrifluoride.

14. A method according to claim 12 wherein said solvent is parachlorobenzotrifluoride.

15. A method according to claim 12 wherein said anisole and said chlorine gas are added separately to said solvent.

16. A method according to claim 15 wherein a small amount of said solvent is first mixed with said anisole.

17. A method of making trichloromethoxybenzene comprising
    (A) continuously separately adding anisole and chlorine gas to a moving stream of benzotrifluoride or parachlorobenzotrifluoride heated to about reflux, where the weight ratio of anisole to said stream is about 0.3 to about 0.5 and said chlorine gas is about 1 to about 5 mole % of stoichiometric;
    (B) exposing said moving stream to ultraviolet light having a wavelength of about 320 to about 340 nm.

18. A method according to claim 17 wherein said solvent is benzotrifluoride.

19. A method according to claim 12 wherein said solvent is parachlorobenzotrifluoride.

20. A method according to claim 11 wherein said metal scavenger is selected from the group consisting of N,N-dialkylalkylamides and ethylenediaminetetraacetic acid.

21. A method according to claim 1 wherein said solvent is dichlorobenzotrifluoride.

* * * * *